United States Patent [19]

Mormann et al.

[11] Patent Number: 4,988,787

[45] Date of Patent: Jan. 29, 1991

[54] ALTERNATING COPOLYMERS, A PROCESS FOR THEIR PREPARATION, AND A METHOD OF USE THEREOF

[75] Inventors: Werner Mormann, Kreuztal; Kerstin Schmalz, Siegen, both of Fed. Rep. of Germany

[73] Assignee: Bayer Aktiengesellschaft, Leverkusen, Fed. Rep. of Germany

[21] Appl. No.: 532,426

[22] Filed: Jun. 4, 1990

[30] Foreign Application Priority Data

Jun. 9, 1989 [DE] Fed. Rep. of Germany ....... 3918893

[51] Int. Cl.$^5$ .................. C08F 226/06; C08F 222/04
[52] U.S. Cl. ...................... 526/262; 526/271; 526/298; 526/300; 526/312; 526/219.6
[58] Field of Search ............ 526/301, 262, 300, 298, 526/271, 310, 312

[56] References Cited

U.S. PATENT DOCUMENTS

| | | | |
|---|---|---|---|
| 2,326,287 | 8/1943 | Coffman | 260/84 |
| 2,334,476 | 11/1943 | Coffman | 260/453 |
| 2,606,892 | 8/1952 | Kropa | 260/80.3 |
| 3,943,112 | 3/1976 | Middleton | 260/80.3 R |
| 3,965,074 | 6/1976 | Middleton | 260/77.5 R |
| 4,351,755 | 9/1982 | Brixius | 524/555 |
| 4,436,855 | 3/1984 | Brixius | 526/214 |

FOREIGN PATENT DOCUMENTS 0336129 10/1989 European Pat. Off. .
3245297 12/1982 Fed. Rep. of Germany .
3245298 12/1982 France .

*Primary Examiner*—C. Warren Ivy
*Assistant Examiner*—M. Nagumo
*Attorney, Agent, or Firm*—Joseph C. Gil; Richard E. L. Henderson

[57] ABSTRACT

The invention relates to alternating copolymers having the formula

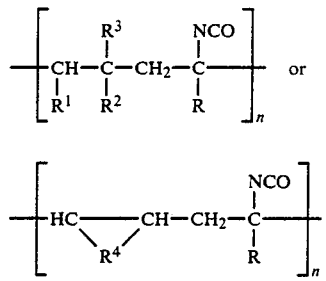

wherein one of $R^1$, $R^2$, and $R^3$ in each repeating unit is hydrogen and the others of $R^1$, $R^2$, and $R^3$ in each repeating unit are CN or $COOR^5$, wherein R5 is $C_1$–$C_8$ alkyl; and n is from 10 to 5,000. This invention further relates to a process for preparing such alternating copolymers by copolymerization of appropriate alkenyl isocyanates and electron deficient olefins.

3 Claims, No Drawings

ALTERNATING COPOLYMERS, A PROCESS FOR THEIR PREPARATION, AND A METHOD OF USE THEREOF

BACKGROUND OF THE INVENTION

The present invention relates to alternating copolymers of alkenyl isocyanates and electron deficient olefins, a process for their preparation, and a method of their use.

Alternating copolymers of alkenyl isocyanates and electron deficient olefins have not previously been described in the literature. Homopolymerization of higher alkenyl isocyantes gives polymers with only a low degree of polymerization.

The object was to provide polymers from alkenyl isocyantes with a high degree of polymerization and which, if appropriate, contain groups of different reactivity that can react independently of one another.

SUMMARY OF THE INVENTION

The invention relates to alternating copolymers having the formula

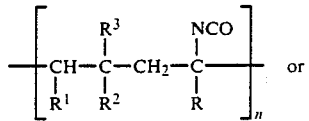

or

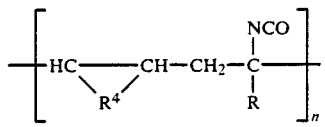

wherein
the "R is hydrogen. $C_1$–$C_6$ alkyl, or ($C_1$–$C_6$ alkyl) ($C_1$–$C_6$ alkane) carboxylate
one of $R^1$, $R^2$, and $R^3$ in each repeating unit is hydrogen and the others of $R^1$, $R^2$, and $R^3$ in each repeating unit are CN or $COOR^5$, wherein $R^5$ is $C_1$–$C_8$ alkyl; and n is from about 10 to about 5,000;
"$R^4$ is —(O=C)—O—(C=O)— or —(O=C)—NH—(C=O)—;
wherein said alternating copolymers are copolymerization products of
(a) alkenyl isocyantes of the formula

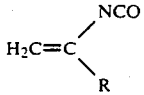

wherein R is hydrogen, $C_1$–$C_6$ alkyl, or ($C_1$–$C_6$ alkyl) ($C_1$–$C_6$ alkane)carboxylate, and
(b) electron deficient olefins of the formula

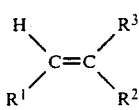

(i)

wherein one of $R^1$, $R^2$, and $R^3$ is hydrogen and the others of $R^1$, $R^2$, and $R^3$ are CN or $COOR^5$, wherein $R^5$ is $C_1$–$C_8$ alkyl; or

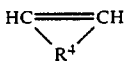

(ii)

wherein $R^4$ is —(O=C)—O—(C=O)— or —(O=C)—NH—(C=O)—.

The invention further relates to a process for the preparation of these alternating copolymers comprising copolymerizing at a temperature between 0° and 100° C. in the presence of initiators
(a) alkenyl isocyanates of the formula

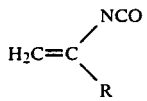

wherein R is hydrogen, $C_1$–$C_6$ alkyl, or ($C_1$–$C_6$ alkyl) ($C_1$–$C_6$ alkane) carboxylate,
with
(b) electron deficient olefins of the formula

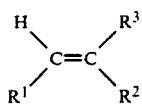

(i)

wherein one of $R^1$, $R^2$, and $R^3$ is hydrogen and the others of $R^1$, $R^2$, and $R^3$ are CN or $COOR^5$, wherein $R^5$ is $C_1$–$C_8$ alkyl; or

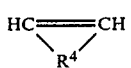

(ii)

wherein $R^4$ is —(O=C)—O—(C=O)— or —(O=C)—NH—(C=O)—.

DETAILED DESCRIPTION OF THE INVENTION

Preferred alternating copolymers are those in which the alkenyl isocyanate component is isopropenyl isocyanate, vinyl isocyanate, or alkyl 4-isocyanato-4-pentenoates and the electron deficient olefin component is maleic anhydride, maleimide, fumaric acid dinitrile, maleic acid dinitrile, maleic dialkyl esters, fumaric dialkyl esters, or cyanoacrylic alkyl esters. Particularly preferred alternating copolymers are those in which the electron deficient olefin component is maleic anhydride.

In the process according to the invention, the copolymerization is preferably carried out in bulk, in solution, or by precipitation polymerization. In a particularly preferred embodiment, copolymerization is carried out at temperatures between 0° C. and 80° C. Preferred initiators include aliphatic azo compounds, peroxides, or known redox initiators:

(4-methoxy-phenylazo)-methyl-malonic acid dinitrile
   $CH_3O—C_6H_4—N=N—C(CH_3)(CN)_2$
Bis-(1-acetoxy-1-phenyl-ethyl)-diazene
   $C_6H_5—C(CH_3)(OC(O)CH_3)—N=N(CH_3C(O)O)(CH_3)C—C_6H_5$
Diphenylmethyl-(1-phenyl-ethyl)-diazene
   $HC(CH_3)(C_6H_5)—N=N—CH(C_6H_5)_2$
Bis-(1-acetoxy-1-alkyl-alkyl)-diazene
   $[R^1R^2C(OC(O)CH_3)]_2N_2$
unsym. 1-Acetoxy-phenylazo-alkane $C_6H_5-N=NCR^1R^2(OC(O)CH_3)$ Azo-bis-isobutane acid-dialkylester
$[(CH_3)_2C(COOR)]_2N_2$ peroxides
$CH_3-C(O)-O-O-SO_2-C_6H_{11}$
$[R-O-C(O)]_2O_2$
$[Cl_2C_6H_3-C(O)]_2O_2$
$(CH_3)_3C-C(O)-O-O-C(CH_3)_3$
$[C_{11}H_{23}-C(O)]_2O_2$
$[C_6H_5-C(O)]_2O_2$
$C_6H_5-C(O)-O-O-C(CH_3)_3$
$[C_6H_5-C(CH_3)_2]_2O_2$ and redox initiators
dibenzoylperoxide/$FeSO_4$
dibenzoylperoxide / 2-oxo-propanol $S_2O_8^{2-}$/ $HSO_3^-$ These alternating copolymers can be used, inter alia, as crosslinking agents for epoxides, polyhydroxy compounds, and diamines in the preparation of crosslinked polymers.

The alternating copolymers of the invention can also be used as carriers for the delivery of medicaments to mammalian patients.

The copolymerization of, for example, isopropenyl isocyanate, methyl 4-isocyanato-4-pentenoate, or vinyl isocyanate with maleic anhydride leads to high yields of alternating copolymers having highly reduced viscosities. The molar ratio of the monomers used in the reaction mixture can be varied within wide limits, for example, from about 1:5 to about 5:1. Even when the monomers are not used in equimolar quantities, the reaction can be conducted with high conversions (that is, almost complete incorporation of the monomer present in the smaller amount) without the alternating sequence in the polymer being affected. Copolymerization using an equimolar ratio of the two monomers is preferred. The polymerization can be carried out, for example, in bulk, in solution, or by precipitation polymerization from a 10% solution in benzene.

The two reactive groups of the unsaturated monomers are stable under the reaction conditions and in the isolated polymers. This stability is surprising because the known reaction between the isocyanate and anhydride groups would have been expected to take place to at least a certain degree and would have led to crosslinked products.

The following example further illustrate details for the preparation of the compositions of this invention. The invention, which is set forth in the foregoing disclosure, is not to be limited either in spirit or scope by these examples. Those skilled in the art will readily understand that known variations of the conditions and processes of the following preparative procedures can be used to prepare these compositions. Unless otherwise noted, all temperatures are degrees Celsius and all percentages are percentages by weight.

EXAMPLES

Example 1

Synthesis of alternating copolymers of isopropenyl isocyanate and maleic anhydride by precipitation polymerization A mixture of 20 ml of benzene, 1.04 g (12.5 mmol) of isopropenyl isocyanate, 1.19 g (12.5 mmol) of maleic anhydride, and 20.4 mg (0.12 mol) of azodiisobutyronitrile ("AIBN") is stirred at 60° C. for 10 hours in a 50 ml flask that has been heated thoroughly in vacuo and then cooled under argon. The polymer starts to precipitate out of the pale yellowcolored solution after about one hour. After ten hours, the precipitate is suction filtered using a fritted glass funnel under an inert gas, rinsed with benzene, and dried at 40° C. under an oil-pump vacuum.

Yield: 1.96 g (88%)

IR (film from acetone): 2270, 1850 and 1780 cm$^{-1}$

Elemental analysis: C, H, and N<0.1% from calculated values

Intrinsic viscosity: 0.44 dl/g (in acetone at 0.264 g/dl)

Examples 2-12

Synthesis of alternating copolymers (general procedure)

The procedure is generally as described under Example 1. The comonomers and AIBN (0.5 mol %, based on the maximum substance which can be polymerized) are weighed out in the molar ratio given in Tables 1-4 and dissolved in benzene, the solution is degassed, and polymerization is carried out 60° C. After the time given in the tables, the precipitated polymer is suction filtered using a fritted glass funnel under an inert gas. The product is extracted by stirring again in benzene and then dried under an oil-pump vacuum.

General properties of the polymers synthesized are as follows:

Solubility: The polymers are soluble in acetone, 2-butanone (methyl ethyl ketone), N,N-dimethylformamide, and N,N-dimethylacetamide.

IR spectra: Clear films of the polymers, which become cloudy on prolonged standing in air (15–30 min), are obtained from an acetone solution. The IR spectra of these films exhibit bands characteristic of the particular structural elements they contain:

Isocyanate 2270 cm$^{-1}$

Methyl ester 1740 cm$^{-1}$

Anhydride 1780 cm$^{-1}$, 1850 cm$^{-1}$

Nitrile 2270 cm$^{-1}$ (overlapped by the isocyanate)

TABLE 1

Composition and properties of alternating copolymers of 2-isocyanato-propene and maleic anhydride

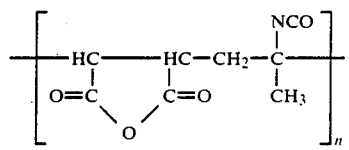

| Example No. | Molar ratio[a] | Reaction time (hr) | Yield[b] (%) | η[c] (dl/g) | $^1$H-NMR (ppm) |
|---|---|---|---|---|---|
| 1 | 1:1 | 8 | 88 | 0.44 | 3.8 (CH, anhydride) |
| 2 | 1:3 | 15 | 80 | 0.31 | 2.8 (CH$_2$) |
| 3 | 3:1 | 15 | 71 | 0.30 | 2.0 (CH$_3$)[d] |
| 4 | 1:2 | 24 | 90 | 0.26 | |
| 5 | 2:1 | 24 | 93 | 0.43 | |

[a]Isocyanate:maleic anhydride
[b]Based on complete conversion of the component present in the lower amount
[c]η denotes intrinsic viscosity
[d]partly overlapped by acetone (solvent)

TABLE 2

Composition and properties of alternating copolymers of methyl 4-isocyanato-4-pentenoate and maleic anhydride $$\left[ \begin{array}{c} \text{HC} \text{—} \text{HC} \text{—} \text{CH}_2 \text{—} \overset{\overset{\displaystyle \text{NCO}}{|}}{\underset{\underset{\displaystyle \text{COOCH}_3}{\displaystyle \text{(CH}_2)_2}}{\text{C}}} \\ \underset{\text{O}}{\text{O=C} \diagdown \diagup \text{C=O}} \end{array} \right]_n$$

| Example No. | Molar ratio[a] | Reaction time (hr) | Yield[b] (%) | $\eta^{(c)}$ (dl/g) | $^1$H-NMR (ppm) |
|---|---|---|---|---|---|
| 6 | 1:1 | 42 | 29 | 0.17 | 3.7 (CH, anhydride) |
| 7 | 1:3 | 42 | 25 | 0.18 | 3.6 (CH$_3$); 2.6 (CH$_2$) |
| 8 | 3:1 | 42 | 15 | 0.17 | |

[a] Isocyanate:maleic anhydride
[b] Based on complete conversion of the component present in the lower amount
[c] $\eta$ denotes intrinsic viscosity

TABLE 3

Composition and properties of alternating copolymers of isocyanato-ethane and maleic anhydride $$\left[ \begin{array}{c} \text{HC} \text{—} \text{HC} \text{—} \text{CH}_2 \text{—} \overset{\overset{\displaystyle \text{NCO}}{|}}{\underset{\underset{\displaystyle \text{H}}{}}{\text{C}}} \\ \underset{\text{O}}{\text{O=C} \diagdown \diagup \text{C=O}} \end{array} \right]_n$$

| Example No. | Molar ratio[a] | Reaction time (hr) | Yield[b] (%) | $\eta^{(c)}$ (dl/g) | $^1$H-NMR (ppm) |
|---|---|---|---|---|---|
| 9 | 1:1 | 15 | 93 | 0.17 | 4.7 (CH, isocyanate) |
| 10 | 1:3 | 42 | 25 | 0.18 | 3.6 (CH, isocyanate) |
| 11 | 3:1 | 42 | 15 | 0.17 | 2.5 (CH$_2$) |

[a] Isocyanate:maleic anhydride
[b] Based on complete conversion of the component present in the lower amount
[c] $\eta$ denote intrinsic viscosity

TABLE 4

Composition and properties of alternating copolymers of isocyanato-propene and fumaric acid dinitrile $$\left[ \text{HC} \text{—} \underset{\underset{\displaystyle \text{CN}}{|}}{\text{CH}} \text{—} \text{CH}_2 \text{—} \overset{\overset{\displaystyle \text{NCO}}{|}}{\underset{\underset{\displaystyle \text{CH}_3}{|}}{\text{C}}} \right]_n$$

with CN CN on the lower left substituents.

| Example No. | Molar ratio[a] | Reaction time (hr) | Yield[b] (%) | $\eta^{(c)}$ (dl/g) | $^1$H-NMR (ppm) |
|---|---|---|---|---|---|
| 12 | 1:1 | 24 | 31 | 0.14 | 3.9 (CH); 2.5 (CH$_2$) 2.0 (CH$_3$)[d] |

[a] Isocyanate:fumaric acid dinitrile
[b] Based on complete conversion of the component present in the lower amount
[c] $\eta$ denotes intrinsic viscosity
[d] Partly overlapped by acetone (solvent)

What is claimed is:

1. An alternating copolymer having the formula

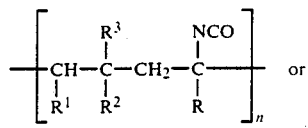

or

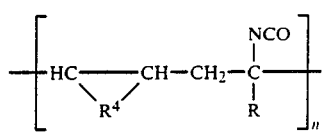

wherein

R is hydrogen, C$_1$–C$_6$ alkyl, or (C$_1$–C$_6$ alkyl) (C$_1$–C$_6$ alkane)carboxylate;

one of R$^1$, R$^2$, and R$^3$ in each repeating unit is hydrogen and the others of R$^1$, R$^2$, and R$^3$ in each repeating unit are CN or COOR$^5$, wherein R$^5$ is C$_1$–C$_8$ alkyl;

R$^4$ is —(O=C)—O—(C=O)— or —(O=C)—NH—(C=O)—; and n is from about 10 to about 5,000;

wherein said alternating copolymer is a copolymerization product of (a) an alkenyl isocyanate of the formula

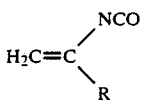

wherein R is hydrogen, C$_1$–C$_6$ alkyl, or (C$_1$–C$_6$ alkyl) (C$_1$–C$_6$ alkane)carboxylate, and (b) an electron deficient olefin of the formula

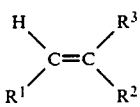 (i)

wherein one of R$^1$, R$^2$, and R$^3$ is hydrogen and the others of R$^1$, R$^2$, and R$^3$ are CN or COOR$^5$, wherein R$^5$ is C$_1$–C$_8$ alkyl; or

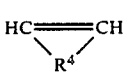 (ii)

wherein R$^4$ is —(O=C)—O—(C=O)— or —(O=C)—NH—(C=O)—.

2. An alternating copolymer according to claim 1 wherein the alkenyl isocyanate is vinyl isocyanate, isopropenyl isocyanate, or (C$_1$–C$_6$ alkyl) 4-isocyanato-4-pentenoate.

3. An alternating copolymer according to claim 1 wherein the electron deficient olefin is maleic anhydride, maleimide, fumaric acid dinitrile, maleic acid dinitrile, a maleic di(C$_1$–C$_8$ alkyl) ester, a fumaric di(C$_1$–C$_8$ alkyl) ester, or a cyanoacrylic (C$_1$–C$_8$ alkyl) ester.

* * * * *